Feb. 4, 1964 J. L. PRICE Plant Pat. 2,350
ALMOND TREE
Filed Oct. 1, 1962
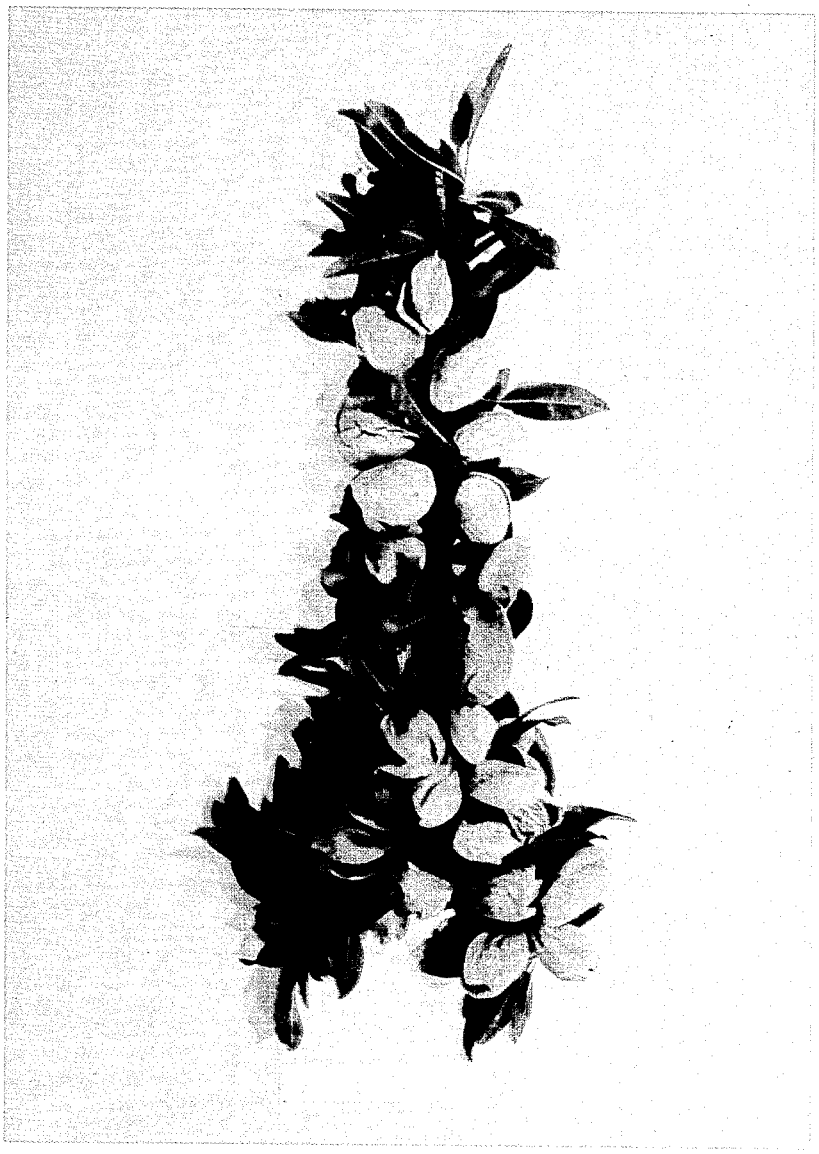
INVENTOR
JOSEPH L. PRICE
BY
Boyken, Molder & Foster.

United States Patent Office

Plant Pat. 2,350
Patented Feb. 4, 1964

2,350
ALMOND TREE

Joseph L. Price, 1306 Court St., Redding, Calif.

Filed Oct. 1, 1962, Ser. No. 227,617
1 Claim. (Cl. Plt.—30)

My new and distinct variety of almond tree, which is herein described and illustrated, was originally discovered by me in 1953 in a 160 acre grove of bearing almond trees in a Nonpareil row. Upon an inspection of each of the trees in this grove during the bearing season, I noticed that the leaves of one tree were a slightly darker color of green than the leaves of other trees in the immediate vicinity. This one tree appeared to be of approximately the same age as the other trees in the grove, and carried appreciably more almonds than the others. While this one tree was similar in general outward appearances to its neighboring trees, a closer inspection immediately set it apart from the others due to the obviously greater number of almonds it carried in cluster-like formation along the branches. This heavy-bearing characteristic of my new variety of almond tree is its most outstanding characteristic.

This same tree was closely watched during subsequent bearing seasons, and particularly during the 1956 season when a severe frost destroyed approximately ninety percent of the almond crop, including the almonds on adjacent trees. However, this tree suffered relatively little injury and produced close to its full normal yield of almonds. This remarkable resistance to cold has been noted in different years in which this tree has consistently borne fruit with litle apparent injury or reduction in volume, whereas other trees under the same conditions have been seriously injured.

My new variety was asexually reproduced in 1957 by budding on peach and bitter almond stock, and also by grafting on bitter almond stock. The young trees show the same characteristics as the original tree. Grafts made on Marianna root have produced a tree bearing extremely thick clusters of almonds, and grafts made on Davey interstock have displayed similar heavy-bearing characteristics. The trees of my new variety provide ample budwood for facilitating further reproduction.

As previously indicated, the most outstanding characteristic of my new variety that distinguishes it from other known varieties is its heavy bearing characteristic. A mature tree of my new variety will bear approximately 2 to 2½ times the amount, by weight, of its closest competitor, the Nonpareil, of the same age.

Specifically, the almonds on trees of my new variety appear in cluster-like formation along the branches, and between twenty-four to thirty mature almonds on each foot of branch length is common. An annual average yield of approximately 4,000 to 6,000 lbs. of unshelled nuts per acre of five year old trees of my new variety, as distinguished from an average yield of approximately 2,000 to 3,000 lbs. of unshelled almonds from the best of other varieties of which I am aware, is a fair estimate of the heavy bearing characteristic from the known yield from the original tree of the new variety and from trees that have been reproduced, by grafting therefrom. Such heavy bearing characteristic is clearly evidenced in the accompanying photograph of a portion of a branch of a three-year old tree of my new variety.

The photograph illustrates a further outstanding characteristic of my new variety, which is that young trees will come into commercial bearing in thre to four years from budding or grafting, whereas other varieties requires five years' time.

The color of the leaves of my new variety tree are a deeper green than the leaves on the Nonparil variety. This is particularly noticeable in viewing the entire tree in relation to adjacent trees of the Nonpareil variety.

The shells of the almonds of my new variety are slightly darker in color than the shells of other soft-shell varieties of which I am aware. The kernels, or meats, appear to be darker than the kernels of the Nonpareil and Davey varieties and slightly lighter in color than those of the Ne Plus Ultra variety.

The average weight of the kernels is 1.08 grams, using the metric conversion of the avoirdupois system, or 26 per ounce. In this respect the kernel of my new variety is similar to or slightly smaller than the Nonpareil variety. The shape of the kernel is similar to that of the Nonpareil, and has an average width to length ratio of 5.3. The average thickness of the kernel is 8.6 mm., which indicates considerable plumpness relative to size.

The almond blossoms of my new variety more closely resemble those of the Nonpareil variety than other known varieties. Specifically, the color of the petal is moderately pink in the bud, becoming light pink, red blush at the base of the petal. The calyx lobes are green, covered with red blush. The pistil is straight and about as long as the stamens. The petal is medium, wavy, and measures approximately 1.6 x 1.1 cm.

In certain cross-pollination trials, pollen from blossoms of my new variety on Nonpareil grave 48% set, and on Texas gave 15% set. Comparatively, pollens from other varieties on my new variety gave the following set: Texas 27%; Nonpareil—11%; Ne Plus Ultra—12%. The favorable results of these trials further illustrate the effectiveness with which my new variety tree may be used for cross-pollinization.

I claim:

A new and distinct variety of almond tree, substantially as herein illustrated and described, characterized particularly by its heavy bearing of almonds carried in cluster-like formation along its branches; by its normal yield which averages 2 to 2½ times that of other varieties of the same age; its exceptional resistance to cold and ability to produce substantially a normal full yield after exposure to heavy frost; its early commercial bearing capabilities in three to four years as compared to five years of other known varieties; and the deeper green color of its leaves as compared to the Nonpareil variety.

No references cited.